(12) United States Patent
Wagner et al.

(10) Patent No.: US 6,605,049 B1
(45) Date of Patent: Aug. 12, 2003

(54) MARKING SYSTEM AND METHOD FOR MEDICAL DEVICES

(75) Inventors: Arno Wagner, Hilden (DE); Wayne E. Cornish, Fallbrook, CA (US); Mark T. Richardson, Escondido, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 14 days.

(21) Appl. No.: 09/748,305

(22) Filed: Dec. 21, 2000

(51) Int. Cl.[7] ............................. A61B 5/00; A61M 25/00
(52) U.S. Cl. ............................................. 600/585
(58) Field of Search .......................... 600/585, 433–435, 600/459, 562–568, 576, 581, 101, 114; 128/897; 604/19, 93.01, 96.01, 164.01, 164.11, 164.18; 606/1, 106, 108, 119, 129, 139, 160, 167, 170, 184, 185, 186, 205, 222; 81/488, 177.1, DIG. 5

(56) References Cited

U.S. PATENT DOCUMENTS

| | | | |
|---|---|---|---|
| 4,538,622 A | | 9/1985 | Samson et al. |
| 4,748,986 A | | 6/1988 | Morrison et al. |
| 4,982,627 A | * | 1/1991 | Johnson .................... 606/41 |
| 5,061,395 A | | 10/1991 | Meng |
| 5,084,022 A | * | 1/1992 | Claude ................... 604/164.13 |
| 5,135,503 A | | 8/1992 | Abrams |
| 5,341,818 A | | 8/1994 | Abrams et al. |
| 5,345,945 A | | 9/1994 | Hodgson et al. |
| 5,573,529 A | * | 11/1996 | Haak et al. .................... 606/1 |
| 5,782,807 A | * | 7/1998 | Falvai et al. ............. 604/164.1 |
| 6,045,623 A | * | 4/2000 | Cannon ......................... 134/8 |
| 6,146,380 A | * | 11/2000 | Racz et al. ................. 81/121.1 |
| 6,248,092 B1 | * | 6/2001 | Miraki et al. ............ 604/96.01 |

* cited by examiner

*Primary Examiner*—Max F. Hindenburg
*Assistant Examiner*—Charles A. Marmor, II
(74) *Attorney, Agent, or Firm*—Fulwider Patton Lee & Utecht, LLP

(57) ABSTRACT

The invention is directed to a system and method of encoded markings on the body of medical devices such as guidewires having limited surface for markings. The markings include indicators of characteristics, such as the design family, the size, and other pertinent specifications. The marking system of the invention comprise an spatially ordered series of marks on the surface of the device, with each mark corresponding to an information or data category. Each mark is coded with a value of the code property which is correlated with and expresses a particular data element within the data category and pertinent to the marked device specimen. The code property value may then be inspected or "read" by the device user to evaluate the data element and obtain information regarding the marked device specimen.

19 Claims, 3 Drawing Sheets

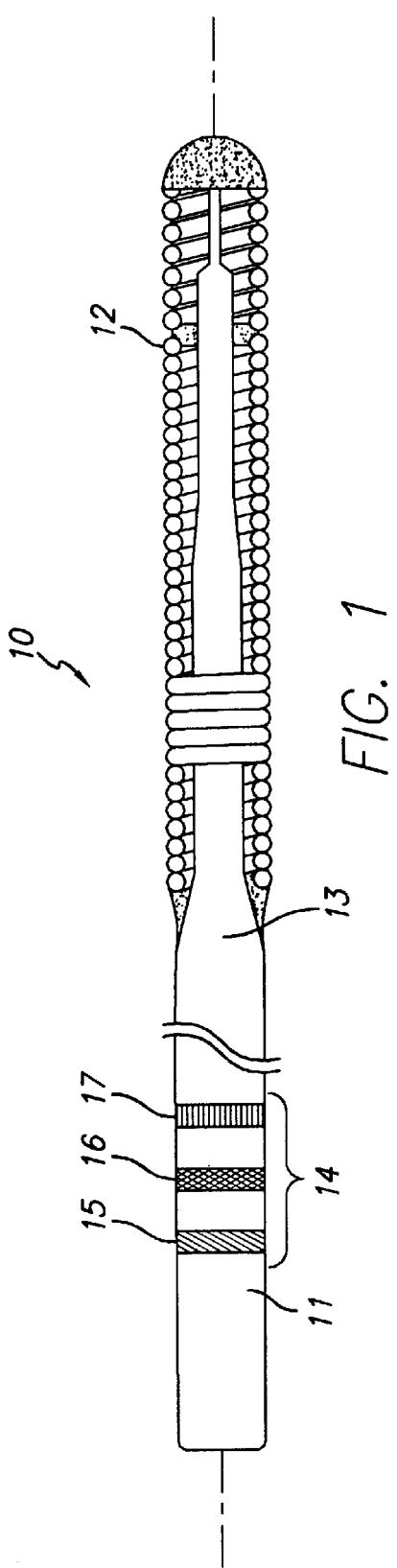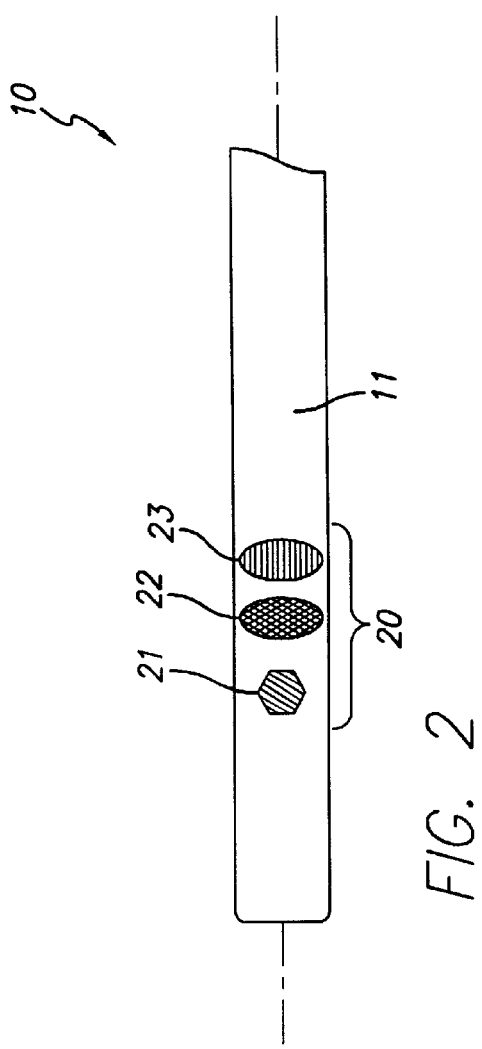

MARKING SYSTEM AND METHOD FOR MEDICAL DEVICES

BACKGROUND OF THE INVENTION

This invention relates to the field of guide-wires for advancing intraluminal devices such as stent delivery catheters, balloon dilatation catheters, atherectomy catheters and the like within body lumens.

In a typical percutaneous coronary procedure, a guiding catheter having a pre-formed distal tip is percutaneously introduced into a patient's peripheral artery, e.g. femoral or brachial artery, by means of a conventional Seldinger technique and advanced therein until the distal tip of the guiding catheter is seated in the ostium of a desired coronary artery. A guide-wire is first advanced by itself through the guiding catheter until the distal tip of the guide-wire extends beyond the arterial location where the procedure is to be performed. A rapid exchange type catheter, such as described in U.S. Pat. No. 5,061,273 (Yock) is mounted onto the proximal portion of the guide-wire which extends out of the proximal end of the guiding catheter which is outside of the patient. The rapid exchange type catheter is advanced over the guide-wire, while the position of the guide-wire is fixed, until the operative means on the rapid exchange type catheter is disposed within the arterial location where the procedure is to be performed. After the procedure the intra-vascular device may be withdrawn from the patient over the guide-wire or the guide-wire repositioned within the coronary anatomy for an additional procedure.

Conventional guide-wires for angioplasty, stent delivery, atherectomy and other intra-vascular procedures usually comprise an elongate core member with one or more tapered segments near the distal end thereof. A shapeable segment of the core member or a shapeable ribbon which is typically secured to the distal extremity of the core member may be utilized to guide the guidewire into desirable arterial branches. A flexible body member, such as a helical coil or a tubular body of polymeric material, is typically disposed about the distal portion of the core member and/or shapeable segment. The leading tip is highly flexible and will not damage or perforate the vessel and the portion behind the distal tip is increasingly stiff which better supports a balloon catheter or similar device which is to be advanced over the guidewire.

Further details of guide-wires, and devices associated therewith for various intervention procedures can be found in U.S. Pat. No. 4,748,986 (Morrison et al.); U.S. Pat. No. 4,538,622 (Samson et al.); U.S. Pat. No. 5,135,503 (Abrams); U.S. Pat. No. 5,341,818 (Abrams et al.); and U.S. Pat. No. 5,345,945 (Hodgson, et al.) which are hereby incorporated herein in their entirety by reference thereto.

During the course of a procedure, several guidewires may be used, and the differences in design of various guidewires are subtle and can be difficult to ascertain by visual inspection, once a guide-wire has been removed from its supplier packaging. For example, it is difficult to easily discriminate between a 0.014" HTF(Hi Torque Floppy)II guide-wire and a 0.014" HTFII Extra Support guide-wire, both of which are manufactured by the present assignee, Advanced Cardiovascular Systems, Inc. These devices are very similar in appearance and the distinctions are not readily seen by the user once they are removed from their packages.

The difficulty in visual identification of guide-wires can lead to a problem of inadvertent mixing and erroneous substitution of guide-wires during the course of a procedure. The size and shape of typical guide-wires do not provide surface area for conventional equipment label plates, such as would typically bear a maker's model identifier, part number, and the like. What has been needed is a system to permit guide-wires to be accurately and quickly identified by surgical personnel during preparation and performance of an intra-vascular procedure.

SUMMARY OF THE INVENTION

The present invention is directed to a system and method of encoded markings for medical devices such as elongated intracorporeal devices, particularly devices such as guide-wires or other intra-vascular or surgical devices which do not have sufficient surface area for conventional marking systems. The marking system provides coded markings on the exterior of the intracorporeal device, preferably on the proximal segment, base or handle portion of the device.

The markings include coded indicators of device characteristics, such as identifying data, qualitative data and/or quantitative data, e.g., the design family, the dimensions, and other pertinent specifications. The coded markings may be repeated on the packaging in which the guide-wire is supplied, together with additional correlated identifying information and specifications. Preferably, a visual display or reference aid setting forth the data/code correlation is also included for placement in the use environment to assist the user in the interpretation of the coded markings, such as a reference chart card mounted on a wall or other convenient surface. The reference aid may also be a computer database, optionally including a search engine to display selected data.

The marking system embodying features of the invention is particularly useful for guide-wire properties which are not externally observable (e.g., type of shaping ribbon encased in flexible body), or for quantitative differences which are only ambiguously directly observable (e.g., small differences in diameter) particularly during the procedure when portions of the device may be within the patient.

The markings of the invention comprise a series of marking elements applied or fixed to the surface of the device such as a guide-wire preferably at a location which will be readily observable during the procedure such as the proximal segment of the guidewire which extends out of the patient during the procedure. The marking elements comprise a plurality of non-overlapping shaped regions or labels on the device surface. Each marking element corresponds to an information or data category. For example, the data categories for a guidewire might be the guidewire type or family, the size, distal tip construction and the like.

The marking elements are arranged upon the device surface in a pre-determined pattern whereby the spatial location or order of each marking element is representative of the corresponding category, i.e., the spatial pattern of the elements is correlated to the sequential order of the categories. For example, the marking elements may be in a linear array, with the sequence of the elements in the array corresponding to the category order. Note that the category order may be arbitrary, the purpose being to establish a one-to-one correspondence between the data category identity and the marking element identity, the correspondence being determinable by the device user upon inspecting the marked device.

Each such shaped marking element region, in turn, has a code property. The code property is expressed (e.g., by being printed, painted, applied, embossed, displayed, and the like)

within the shaped marking element region in any selected one of a range of code property "values", each value of the code property corresponding to a particular data "value" within the category of the marking element. The code property value may then be inspected or "read" by the device user to obtain information or data pertinent to the guide-wire or other device. Note that the term "value" as used herein may refer to various types of data or characteristics, both quantitative and qualitative.

Each data category includes a plurality of data elements relating to the category, each data element being one value of a range of values relevant to device class. The data elements may be model data identifiers, qualitative data values and/or quantitative data values pertaining to a range of different specimens (e.g., a range of models, a range of design types identifiers, a range of dimensional values, and the like). Within each category, each data element is associated or correlated with a specific, distinct code property value.

Thus, each such mark is coded to convey a single data element, i.e., each mark displays a value of the code property which corresponds to and represents the expressed data element value. Each mark may convey an independent data element via its code property (e.g., a, single code element to specify design type). Alternatively, two or more adjacent marks may be "read" in combination so that their combined data elements conveys an integrated item of information (e.g., multiple digits read together as a single numerical value).

In one marking system embodiment, the marks comprise a plurality of bands about the circumference of the guide-wire proximal segment, shaped as rings of sufficient width to be clearly visible upon user inspection. The bands or rings are disposed in a linear array along the longitudinal axis of the proximal segment, preferably with spacing so that each ring is seen by the user distinct from adjacent rings. Each ring represents a data or information category with respect to the guide-wire or device (e.g., design type, diameter and the like)

A preferred code property is color, and thus each marking element region has a selected color ("color value"). The term "color" is used herein broadly to mean a visually distinct color expression, whether due to a distinct hue, saturation level, and the like or combinations thereof. In the example of band or ring-shaped marking elements, on each band the selected color is printed, painted, applied or displayed. The colors are preferably selected so as to be highly visible and distinct under low light levels.

For example, for a category "guide-wire design type", the data elements may be a range of different guide-wire design type designations or "values", each such design type value being associated with a corresponding color or value. For the category "diameter", the data elements may be a range of different diameter values, with each such value being associated with a distinct color. Thus, for the marking elements placed upon any particular guide-wire or device specimen, for each category the particular color is selected that is associated with the true or correct data element value for the particular specimen.

Note, however, that the same color may be assigned to more than one data element, if the data elements are in different categories. For example, in the case of numerical data, it is convenient for the user if the same color is assigned to the same digital values in each category expressing numerical data.

Alternatively or in addition to color coding, other code properties may be employed in the marking elements, such as distinctive visual patterns within the shaped region, distinctive tactile textures, and the like. If desired, shape of the marking element may itself be a code property. It is preferred that a single code property be employed for all marking elements, although alternatively, different code properties may be used for different categories/marking elements.

Alternatively or additionally, the marking elements may be shapes other than bands about the circumference of the proximal segment. For example, marking element shapes may be shaped as partial circumference bands, circles, ellipses or hexagons, and the like, or combinations of different shapes in the array.

The shape, geometry and/or size of each marking element may be the same, or may be different. For user mnemonic convenience, different categories of data may be conveyed to the user by marking element of a shape which is correlated with the category. For example, the design type of the guide-wire may be conveyed by a wider band, while the diameter may be conveyed by one or more relatively narrow bands. Thus, while the order of a particular marking element in the spatial sequence along the guide-wire body can itself convey unambiguously the particular category of the marking element (e.g., first band codes the design type, second and third bands code the diameter), the use of particular shapes to represent particular categories can reinforce this distinction in the user's mind.

It may be seen that the logical relationship between selected device characteristics and the categories and data elements may be expressed in the form of a correlation table, data array, or equivalent logical association. Each category is linked to a marking element. For each such linked category/marking element pair, a logical array may be established linking each data element value with a corresponding code value. Thus in the previous guide-wire example, in the category of "design type", the category is linked to a particular marking element (e.g., the first band). In turn, each of the plurality of specified design types is linked to a selected color code. Similarly, in the category of "diameter", each specified diameter value is linked to a selected color. The term correlation table is used in this regard to mean the logical association of elements as described, whether or not expressed in written form, computer memory, and the like.

BRIEF DESCRIPTION OF THE DRAWINGS

FIG. 1 is an elevation view a guide-wire embodying features of the marking system of the invention.

FIG. 2 is an elevation view a guide-wire embodying alternative features of the marking system of the invention.

DETAILED DESCRIPTION OF THE INVENTION

Figure 3:
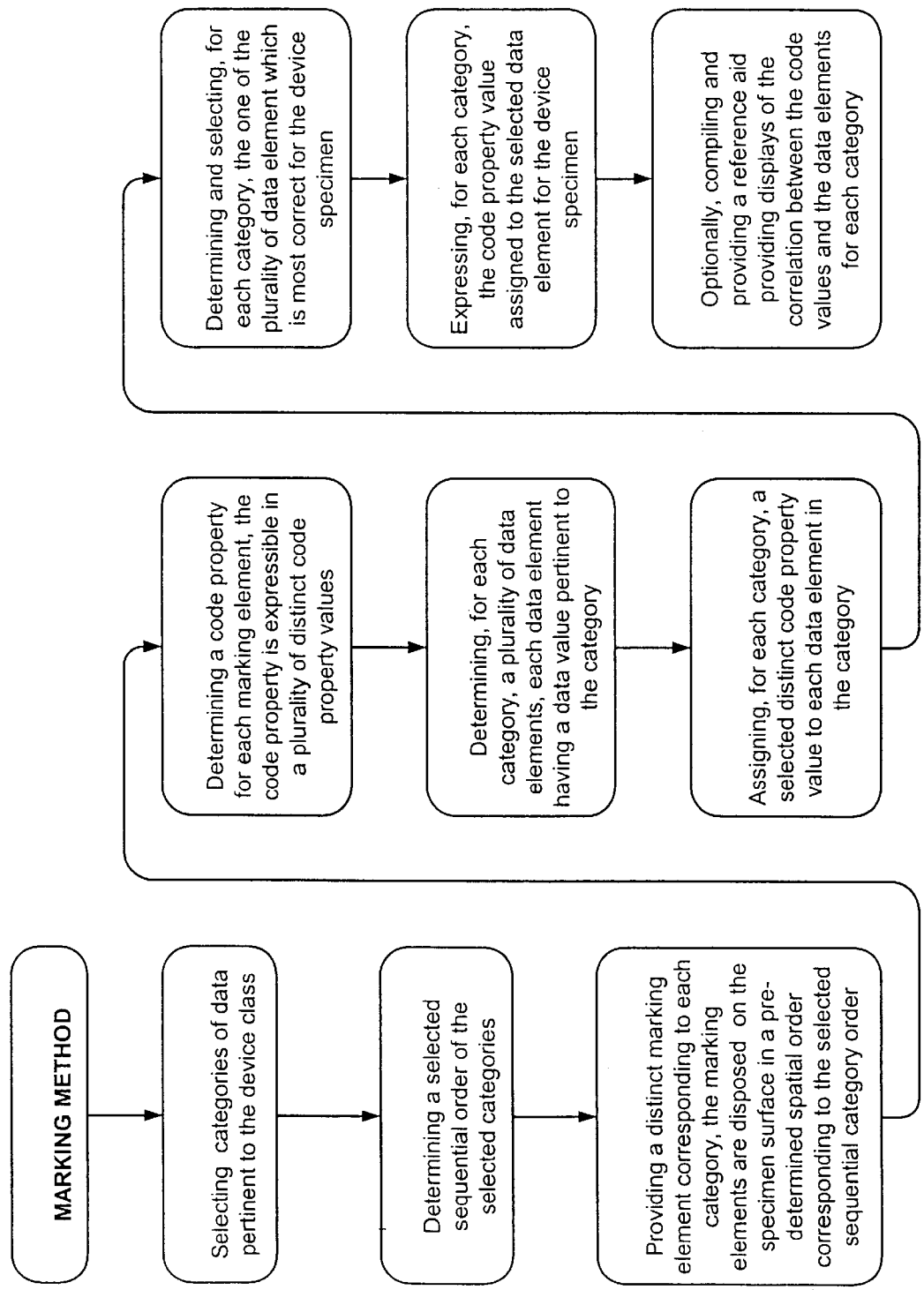
FIG. 3 is a flowchart showing the method of the invention for marking a specimen of a guide-wire or other device.

FIG. 1 is an elevation view a guide-wire 10 showing an example of a marking system embodying features of the invention. The guide-wire 10 comprises a proximal section 11 of generally round cross-section, a distal section 12, and a tapered intermediate section 13. The marking system 14 comprises a plurality of marks comprising readily distinctive circumferential bands 15, 16 and 17. Three bands are shown, by way of example, although there may be more or fewer.

The bands are each of a selected color which is distinct from the color of the proximal section 11 of the guide-wire 10. Other distinguishable characteristic such as size, appearance or tactile feel may be utilized in lieu of color. The bands 15, 16 and 17 are shown of equal width shape and of equally spaced order, but they need not be of equal width or equally spaced.

The bands 15, 16 and 17 may each represent a distinct property category of the guide-wire, e.g., design type, diameter, length, and the like. Each band may be of a selected color of a range of colors, wherein each color of the range represents a value within the category represented by the band. The color ranges of adjacent bands may overlap, where the position of the band determines the property category and the color the value within the category.

For example, if the first band 15 (most proximal) represents the design type of the distal shapeable segment (not shown in FIG. 1) of the guidewire 10, and the second band 16 represents the diameter of the distal core segment 12, then a given color (e.g., blue) will have a clear meaning when present in band 15 distinct from its meaning when present in band 16.

Alternatively, adjacent bands may be related so that the combination and/or order of band colors represent a distinct meaning relating to the guide-wire properties. In this regard, the adjacent bands may represent successive digits in a numerical value descriptive of the guide-wire.

Clearly, there is a broad range of coded information which may be associated with the colors of bands and the number of bands. It is preferred that the number of bands be a small enough number for the order of a given band to be immediately distinct without conscious counting, e.g., three to four bands. It is also preferred that the number of colors used be relatively small, to avoid fine distinctions of shade and to assist rapid memorization. Any of a wide variety of qualitative, quantitative and proprietary data may be so encoded and marked upon the guide-wire.

Table 1 below shows a guide-wire code correlation table for an example by way of illustration of a three-band guide-wire marking system including both qualitative and multi-digit quantitative information.

TABLE 1

Example Of Guide-wire Data/Category Code Correlation

| First Band Shapeable Segment Type | | Second Band Diameter (0.01 in.) | | Third Band Diameter (0.001 in.) | |
| --- | --- | --- | --- | --- | --- |
| Value | Color Code | Value | Color Code | Value | Color Code |
| Round Tapered | Red | 0 | Black | 0 | Black |
| Round Constant | Green | 1 | White | 1 | White |
| Flat Tapered | Blue | 2 | Red | 2 | Red |
| Flat Constant | Yellow | 3 | Green | 3 | Green |
| | | 4 | Blue | 4 | Blue |
| | | 5 | Yellow | 5 | Yellow |
| | | 6 | Maroon | 6 | Maroon |
| | | 7 | Turquoise | 7 | Turquoise |
| | | 8 | Brown | 8 | Brown |
| | | 9 | Olive | 9 | Olive |

In example of Table 1 above, a guide-wire with a round tapered shapeable segment and a distal core diameter of 0.014 inch (0.36 mm) having the marking system shown in FIG. 1 may be coded as follows: The three-band color combination of Red, White, and Blue, wherein the red color of the first band (15 in FIG. 1) represents a round tapered shapeable segment, the white color of the second band (16) represents a first digit value of distal segment diameter of 1×0.01 in., and the blue color of the third band (17) represents a second digit value of distal segment diameter of 4×0.001 in. Thus, the example guide-wire has a round, tapered shapeable segment and diameter of 0.01+0.004 =0.014 inches.

FIG. 2 is a partial elevational view of the proximal section 11 of guide-wire 10 showing an alternative marking system 20 embodying features of the invention. The example guide-wire 10 is structurally the same as the example guide-wire 10 of FIG. 1, and the same numbers reference its elements as appropriate. The alternative marking system comprises a plurality of marks comprising colored shapes 21, 22 and 23. In this example, the first mark 21 has a hexagonal shape and the second and third marks 22 and 23 each have an elliptical shape. By analogy to the example of Table 1 above, the hexagonal mark 20 may represent a "shapeable segment type" category, while the elliptical elements 22 and 23 may represent the first and second digit categories respectively, to express in combination the two-figure value of the distal guide-wire segment diameter. The difference in shape of the marks serves as a mnemonic indicator to the respective categories.

The marks 21, 22 and 23 are disposed in a generally linear array-like spatial order, but the spatial order need not be linear. Alternative non-linear pre-determined spatial orders corresponding to category sequence order may be employed.

FIG. 3 is a flowchart showing an exemplary method embodying features of the invention for marking a specimen of a class of guide-wires or other intra-vascular or surgical devices. The method comprises the following operations which may be performed in any order:

Selecting at least one category of data or information pertinent to the subject device class, e.g., types of guide-wires, sizes of guide-wires as previously described.

Selecting a sequential order for the categories;

Providing on the surface of the device a distinct mark corresponding to each category, which comprises a region of pre-determined shape. The marks are disposed on the body surface in a pre-determined spatial order corresponding to the selected sequential order of the respective categories.

Selecting an identifiable code property (e.g. color, shape etc.) for each mark which is capable of being expressed in a plurality of distinct code property values.

For each category, determining a plurality of data elements for the code property which have a data value pertinent to the particular category and preferably collectively characterizing the range of different types or values present in the class of device;

For each category, assigning a selected code property value to each data element in the category which is distinct from the code property value assigned to any other data element in the category.

For each category, determining which of the plurality of data elements is most correct with respect to the characteristics of the device specimen and selecting this data element.

For each category, expressing in the corresponding mark the code property value assigned to the selected data element for the device specimen.

Optionally, compiling and providing a reference aid which displays the correlation between the code values and the data elements for each category.

Figure 4:
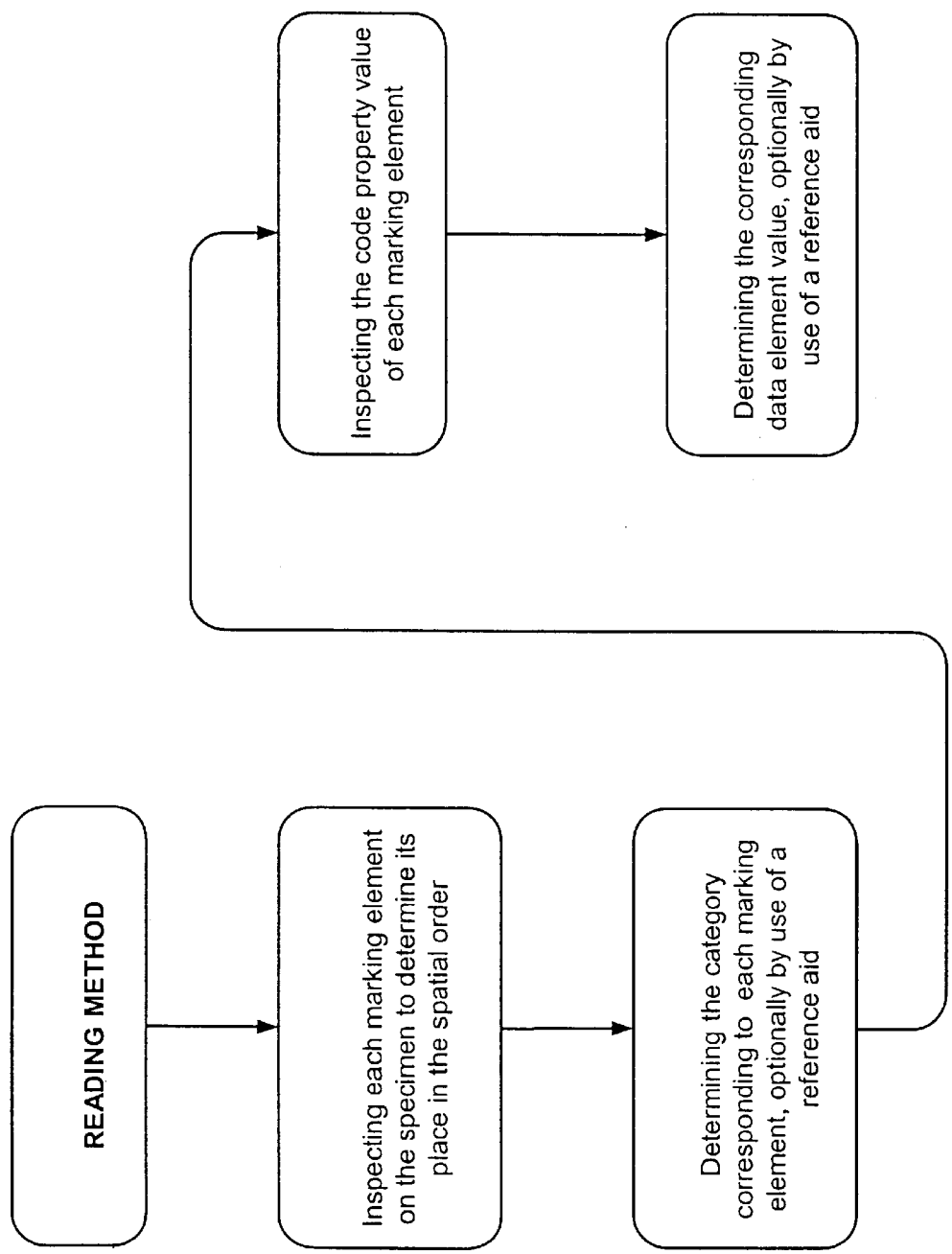
FIG. 4 is a flowchart showing the method of the invention for reading the markings made by the method of FIG. 3.

FIG. 4 is a flowchart showing an exemplary method embodying features of the invention for reading the markings applied to a device as described above. The reading method comprises the following operations which may be performed in any operative order.

Each mark on the device body is inspected in order to determine its place in the spatial order.

For each mark, the corresponding data element value is then determined from the code property value, optionally by use of a reference aid.

Each mark on the device body is then inspected to determine its code property value.

For each mark, the corresponding data element value is then determined form the code property value, optionally by use of a reference aid.

It may be seen that the marking system embodying features of the invention permits a medical device to be coded in a manner that is distinctly visible and which provides unambiguous information to medical personnel. Note that although the marking system and method embodying If features of the invention have been described herein primarily with respect to guidewire, they may be applied to a variety of intracorporeal therapeutic and diagnostic devices having insufficient surface areas for conventional markings. Moreover, while particular embodiments of the invention have been illustrated and described, it will be apparent that various modifications can be made without departing from the spirit and scope of the invention. Accordingly, it is not intended that the invention be limited, except as by the appended claims.

What is claimed is:

1. A method of marking a specimen of a guide wire having limited surface area to express information about the specimen, comprising:

selecting a plurality of information categories representative of data pertinent to the guide wire;

providing a distinct marking element on the surface of the specimen at a proximal end only corresponding to each information category;

determining a code property for each marking element which is expressible in a plurality of distinct code property values;

determining, for each category, a plurality of data elements, each data element having a data value pertinent to the respective category;

assigning, for each category, a distinct code property value to each data element in the category;

selecting, for each category, one of the plurality of data elements of the respective category, which represents information regarding the specimen; and for each marking element, expressing on the respective marking element the code property value assigned to the selected data element of the corresponding category.

2. The method of claim 1 wherein each marking element is disposed on the surface of the specimen in a spatial pattern.

3. The method of claim 2, wherein the step of providing a distinct marking element on the surface includes disposing the elements in a generally linear spatial order corresponding to the category sequence order.

4. The method of claim 3, further comprising the step of compiling and providing a reference aid including at least one of:

a) information regarding correlation between the marking element spatial order and the corresponding category sequence order; and b) information regarding correlation between the assigned code property values and the corresponding data elements for each category.

5. The method of claim 3, wherein the step of providing a distinct marking element corresponding to each category includes that the spatial order of the marking elements is characterized by disposing the marking elements in a generally linear array on the surface.

6. The method of claim 3, wherein the code properties include visibly distinct colors.

7. The method of claim 6, wherein the specimen includes a generally round elongated proximal segment having a longitudinal axis and marking elements comprising a plurality of bands are disposed longitudinally on the surface.

8. The method of claim 7, wherein marking elements are disposed on the proximal segment of the guide wire specimen.

9. The method of claim 8, wherein the step of selecting a plurality of categories of data includes selecting at least a category representative of guide wire distal segment diameter.

10. The method of claim 8, wherein the step of selecting a plurality of categories of data includes selecting at least two categories representative of different digital values of a multi-digit expression of a guide wire property.

11. The method of claim 1, wherein the step of selecting one of the plurality of data elements for each category includes determining the one of the plurality of data elements which is most representative of the specimen.

12. A marked device specimen of a class of guide wires, the specimen being marked to express information about the specimen, the specimen having a body surface, the specimen comprising:

a) a plurality of distinct marks disposed on the body surface of the guide wire in a particular sequence, with each of the marks representative of one of a plurality of selected data categories pertinent to the device class, wherein the distinct marks are disposed only at the proximal end of the guide wire; and b) each of the marks displaying a selected code property value, which is assigned to represent a data element value pertinent to the specimen.

13. The marked device specimen of claim 12, wherein the particular sequence of the marks is characterized by a generally linear array on the body surface.

14. The marked device specimen of claim 12, wherein the selected code property value includes a visibly distinct color.

15. The marked device specimen of claim 14, wherein:

a) the body includes a generally rounded elongate proximal segment having a longitudinal axis; and a) the marks comprise a plurality of bands disposed on the rounded elongate proximal segment and extending substantially around the circumference of the rounded elongate proximal segment.

16. The marked device specimen of claim 15, wherein the marking bands are spaced apart along the longitudinal axis of the rounded elongate proximal segment.

17. The marked device specimen of claim 15, wherein at least one of the marks is representative of a category of guide wire design type.

18. The marked device specimen of claim 15, wherein at least one of marks is representative of a category of guide wire distal segment diameter.

19. The marked device specimen of claim 15, wherein at least two of the plurality of marks are representative of different digital values of a multi-digit expression of a guide wire property.

* * * * *

UNITED STATES PATENT AND TRADEMARK OFFICE
CERTIFICATE OF CORRECTION

PATENT NO. : 6,605,049 B1
DATED : August 12, 2003
INVENTOR(S) : Arno Wagner et al.

It is certified that error appears in the above-identified patent and that said Letters Patent is hereby corrected as shown below:

Column 7,
Line 9, change "form:" to read -- from --.

Signed and Sealed this

Seventh Day of October, 2003

JAMES E. ROGAN
*Director of the United States Patent and Trademark Office*